United States Patent
Moore et al.

(10) Patent No.: US 6,228,650 B1
(45) Date of Patent: May 8, 2001

(54) ACID CATALYST REGENERATION CONTROL

(75) Inventors: William P. Moore, Lake Jackson; Mark A. Clark, Sweeny, both of TX (US); Bruce B. Randolph, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/206,801

(22) Filed: Dec. 7, 1998

Related U.S. Application Data
(60) Provisional application No. 60/069,866, filed on Dec. 17, 1997.

(51) Int. Cl.[7] .......................... G01N 21/00; G01N 35/08
(52) U.S. Cl. .......................... 436/55; 250/338.1; 422/62; 436/37; 436/39; 436/40; 436/60; 436/61; 436/100; 436/101
(58) Field of Search .................................. 422/62; 436/37, 436/39, 40, 100, 101, 60, 61, 55; 250/338.1, 338.5, 339.01, 339.06, 339.07, 339.1, 339.12

(56) References Cited

U.S. PATENT DOCUMENTS

| | | | |
|---|---|---|---|
| 3,002,818 | * 10/1961 | Berger . | |
| 3,793,394 | 2/1974 | Chapman | 585/723 |
| 4,317,795 | * 3/1982 | Makovec et al. | 422/62 |
| 4,473,442 | 9/1984 | Funk et al. | 203/2 |
| 5,407,830 | * 4/1995 | Altman et al. | 436/55 |
| 5,527,980 | 6/1996 | Carlson | 585/730 |
| 5,583,049 | * 12/1996 | Altman et al. | 436/55 |
| 5,681,749 | 10/1997 | Ramamoorthy | 436/55 |

FOREIGN PATENT DOCUMENTS 8-301793 * 11/1996 (JP) .

* cited by examiner

*Primary Examiner*—Arlen Soderquist
(74) *Attorney, Agent, or Firm*—George E. Bogatie

(57) ABSTRACT

In an HF alkylation process where an acid catalyst regeneration column separates HF acid from ASO and water to provide regenerated catalyst for a catalyst circulation stream, and where buildup of ASO in the catalyst circulation stream is encountered, an improved control scheme uses an on-line analyzer/controller to maintain desired concentrations of HF acid, or ASO or water in the catalyst circulation stream. In one embodoment, a continuously flowing catalyst slip stream is piped to the analyzer/controller for simultaneously determining concentration of HF acid, ASO and water, and in a preferred embodiment the ASO concentration is maintained at a desired low level by manipulating temperature of a stripping fluid charged to a lower section of the column. An alternate manipulated variable is temperature of the acid catalyst feed to the regenerator column. Alternate controlled variables are the HF acid, and water concentration in the catalyst circulation stream.

30 Claims, 3 Drawing Sheets

ACID CATALYST REGENERATION CONTROL

This application is a continuation of provisional application Ser. No. 60/069,866 filed Dec. 17, 1997.

The present invention relates to chemical process control using near infrared (NIR) spectroscopy instrumentation, and more particularly to predicting and controlling acid catalyst strength to improve a hydrocarbon alkylation process.

BACKGROUND OF THE INVENTION

Hydrogen fluoride (HF) alkylation is an important refinery process in which isobutane is reacted with olefins to produce highly-branched isoparaffins as illustrated in FIG. 1 for use in gasoline blending. In this process, hydrofluoric (HF) acid functions as the catalyst and recirculates through the reactor. The recirculating HF acid catalyst is not pure; it contains a small amount of water and a reaction byproduct called acid-soluble oil. The catalyst is also saturated with the hydrocarbons involved in the process (e.g., alkylate and isobutane). In the HF alkylation process, it is important to monitor and control the purity of the catalyst since excessive amounts of water and acid-soluble-oil (ASO) have deleterious consequences: Excessive water, for example, can cause rapid corrosion of the carbon steel reactor.

Controlling the composition of the catalyst requires knowing the concentrations of HF acid, water, and ASO in the recirculating catalyst. Therefore, operators must take samples of the catalyst periodically and have these components measured by classical analytical techniques. There are several problems associated with this approach: First of all, HF acid will cause serious burns if it contacts skin. Because of this hazard, collecting and analyzing these samples carries potential for injury. Another problem is that the analytical methods used for these measurements lack precision, especially the method for ASO. This often makes it difficult to determine if the composition of the catalyst has changed from sample to sample. Finally, samples are drawn from the reactor only once or twice a day, and the analyses require several hours. This makes it difficult to follow the composition of the catalyst when processing changes do occur.

In the past few years, there has been a great deal of interest in on-line monitoring of various refinery process streams. In part, this interest has been spurred by advances in analytical technology that have greatly expanded the capabilities for process monitoring.

Accordingly an object of this invention is to continuously analyze process streams containing HF acid catalyst.

A more specific object is to use improved control schemes in acid catalyst processes, which result in tighter process controls, higher productivity and improved product quality.

Yet another object of this invention is to reduce exposure of refining personnel to hazardous process chemicals.

SUMMARY OF THE INVENTION

According to this invention, the foregoing and other objects and advantages are achieved in a method and apparatus for controlling an HF acid regenerator column, which employs an isobutane stripping charge in effecting separation of HF acid, ASO and $H_2O$. The HF acid regenerator, which is one column in an HF alkylation process which also includes a reactor, a settler vessel, a source of fresh HF acid, and a suitable hydrocarbon stream, employs an NIR triple or quadruple component analyzer/controller configured to control acid catalyst strength. In a first embodiment of a regeneration control system the ASO/$H_2O$ output of the NIR triple-component analyzer maintains a desired ASO/$H_2O$ concentration in the catalyst recirculating through the reactor by manipulating the temperature of the stripping isobutane charge to the regeneration column. This scheme allows more ASO/$H_2O$ to be withdrawn in the regenerator bottoms stream as the stripping fluid temperature is reduced. In another embodiment of the control scheme, HF/ASO output values from the NIR analyzer/controller manipulate temperature of the regenerator feed heater to increase HF/ASO content in the regenerator bottoms stream as the spent acid catalyst feed temperature is lowered. In a third embodiment of the regenerator control scheme, which would be employed when sulfolane additive is present in the process acid catalyst, the $H_2O$ output from the NIR analyzer/controller manipulates flow rate of a side draw stream such that an increased draw rate reduces $H_2O$ levels in the process catalyst.

Other objects and advantages of this invention will be apparent from the foregoing brief description of the invention and the appended claims as well as the detailed description and the drawings which are briefly described as follows:

DETAILED DESCRIPTION OF THE INVENTION

Near-Infrared Spectroscopy

Figure 1:
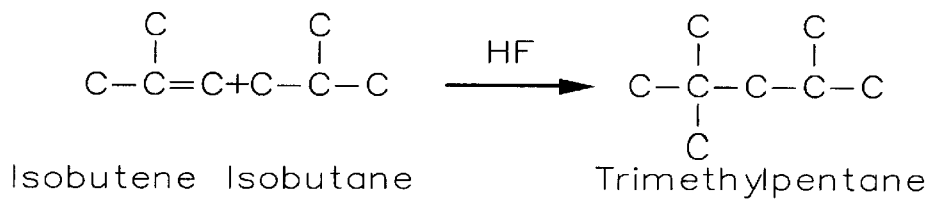
FIG. 1 is an illustration of a chemical formula for producing an alkylate.
Figure 2:
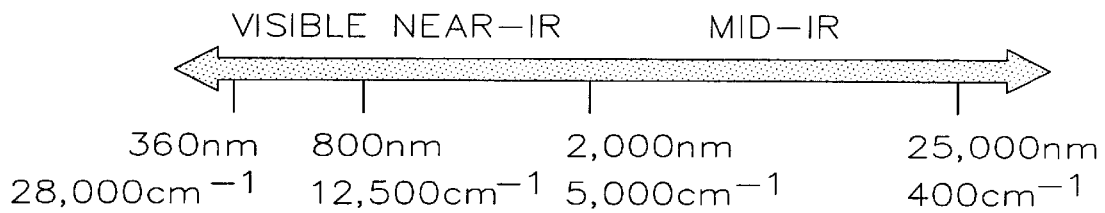
FIG. 2 is a graphical form used to illustrate the NIR region of the electromagnetic spectrum.

The method and apparatus described in this specification involves a process control technique based on near-infrared (NIR) spectroscopy, which uses electromagnetic radiation in the region shown in FIG. 2 to provide concentration outputs for triple components. This region of the spectrum lies between the visible region where our eyes function and the mid-infrared region where conventional infrared spectroscopy is performed.

In NIR spectroscopy the radiation from a halogen lamp is caused to pass through a sample, which in on-line analyzers is continuously flowing through a cell. After the radiation passes through the sample, it is dispersed into its various wavelengths. Finally, the various wavelengths are detected and a spectrum produced in which the amount of radiation absorbed is plotted as a function of wavelength.

Figure 3:
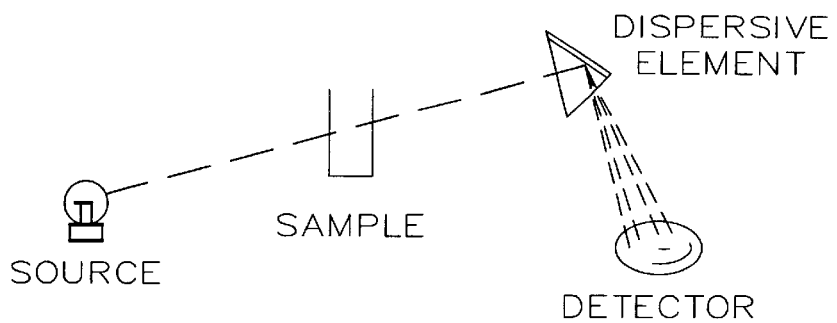
FIG. 3 is a schematic diagram illustrating key components used for NIR spectroscopy.
Figure 4:
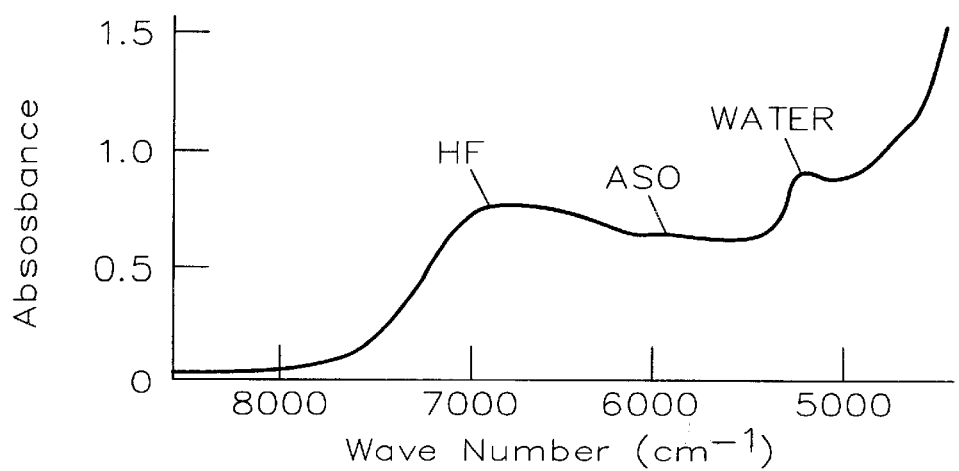
FIG. 4 is a graph showing NIR absorbance spectrum of HF process acid catalyst.

The key components of NIR spectroscopy are illustrated in FIG. 3: As in mid-IR spectroscopy, NIR spectra reflect the chemical structure of the compound(s) measured. In other words, each different chemical will have a unique absorption spectrum. NIR measurement times are fast, with results typically updated every 1–3 min., and NIR spectroscopy is inherently very precise. This is very important in process monitoring where detecting small changes in the process and following the associated trends is often of primary interest. NIR instrumentation and optics are very rugged, and instruments often have only one moving part, and also robust optic materials such as quartz and sapphire can be used. Compatibility with quartz optics allows optical fibers to be used to convey NIR radiation from the spectrometer to a remote sample point. This provides a great deal of flexibility in how the analyzer is interfaced with the process. Optical multiplexing can be used in conjunction with fiber optics to monitor several sampling points with the same spectrometer. The combination of all of these features makes NIR spectroscopy one of the very best analytical techniques for on-line process monitoring. A suitable on-line process analyzer for Fourier transform—IR application, is available from a company called Applied Automation Inc. (AAI), Inc. Bartlesville, Okla. 74004. This analyzer includes software that controls a sampling system, cell washing etc. in addition to obtaining spectral data for triple or quadruple components.

Analyzer Configuration

Figure 5:
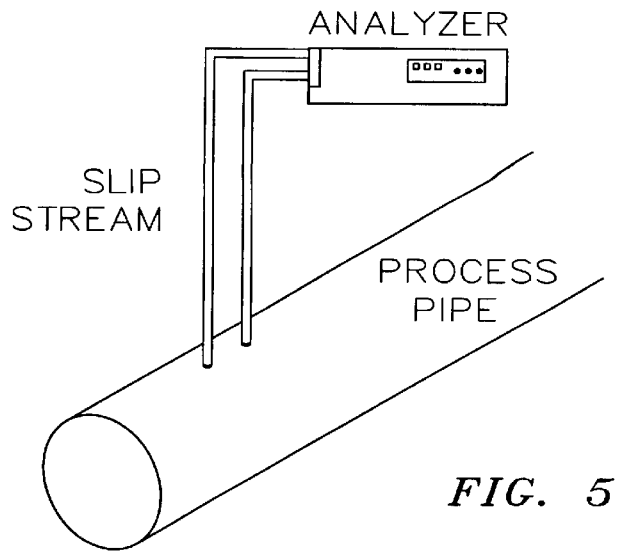
FIG. 5 is a schematic diagram illustrating an NIR analyzer interfaced to a process.

As mentioned above, NIR analyzers can be interfaced with a process in a wide variety of configurations. One approach, shown in FIG. 5, involves running a slip stream from the process pipe to the analyzer. This approach is analogous to that used with gas chromatographic analyzers where the sample is brought to the analyzer. There are significant design limitations in this approach: The analyzer needs to be close to the sample point and the analyzer design must provide appropriate isolation between the sample cell and the electronics. On the other hand, this design offers some significant advantages: It allows sample conditioning such as filtering or thermostating as well as automated cell washing. In addition, the spectra produced are of the highest quality since they are free of any spectral artifacts that may be caused by optical fiber.

Figure 6:
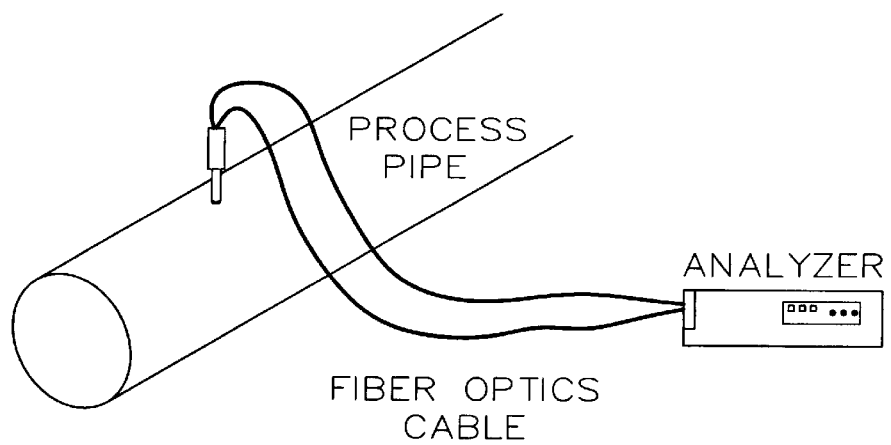
FIG. 6 is a view similar to FIG. 5 illustrating an alternate configuration.

Another interface configuration is shown in FIG. 6. Here a spectroscopic probe is inserted directly into a process stream. This configuration has the advantage of simplicity. It also allows the analyzer to be located away from the measurement point through the use of optical fiber. The major disadvantage is that it does not allow any sample conditioning. The probe must also be removed periodically for cleaning, which can also present a disadvantage.

Figure 7:
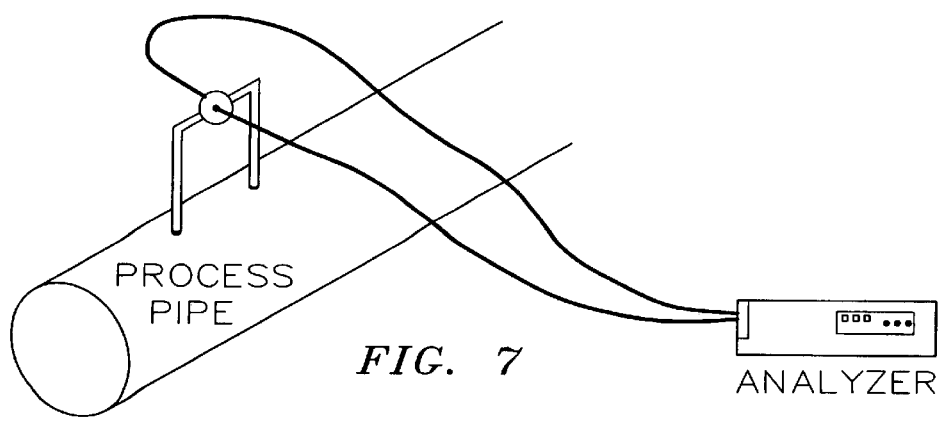
FIG. 7 is a view similar to FIG. 5 illustrating a second alternate configuration.

The third configuration, shown in FIG. 7, represents a compromise approach with design features common to the previous two configurations. In this approach, the sample cell is located in a slip stream, and thus sample conditioning is possible. Using an optical fiber interface maintains the ability to locate the analyzer in a remote location.

Feedback control systems are widely used to achieve efficient operation in HF alkylation processes by controlling the perturbations normally encountered in the operation of various units. Such perturbations occur for example due to upsets in the operation of certain equipment in the plant, adjustment of operating conditions by plant operators, changes in production rates, and the like. In these feedback control systems a plurality of parameters such as pressures, temperatures, flow rates, concentrations and liquid levels at specific locations in the process are controlled at desired set points by measuring each parameter, determining the deviation of each parameter from its set point and using the value of the deviation to manipulate a final control element such as a valve located somewhere in the process that will minimize the deviation of each measured parameter from its set point.

Figure 8:
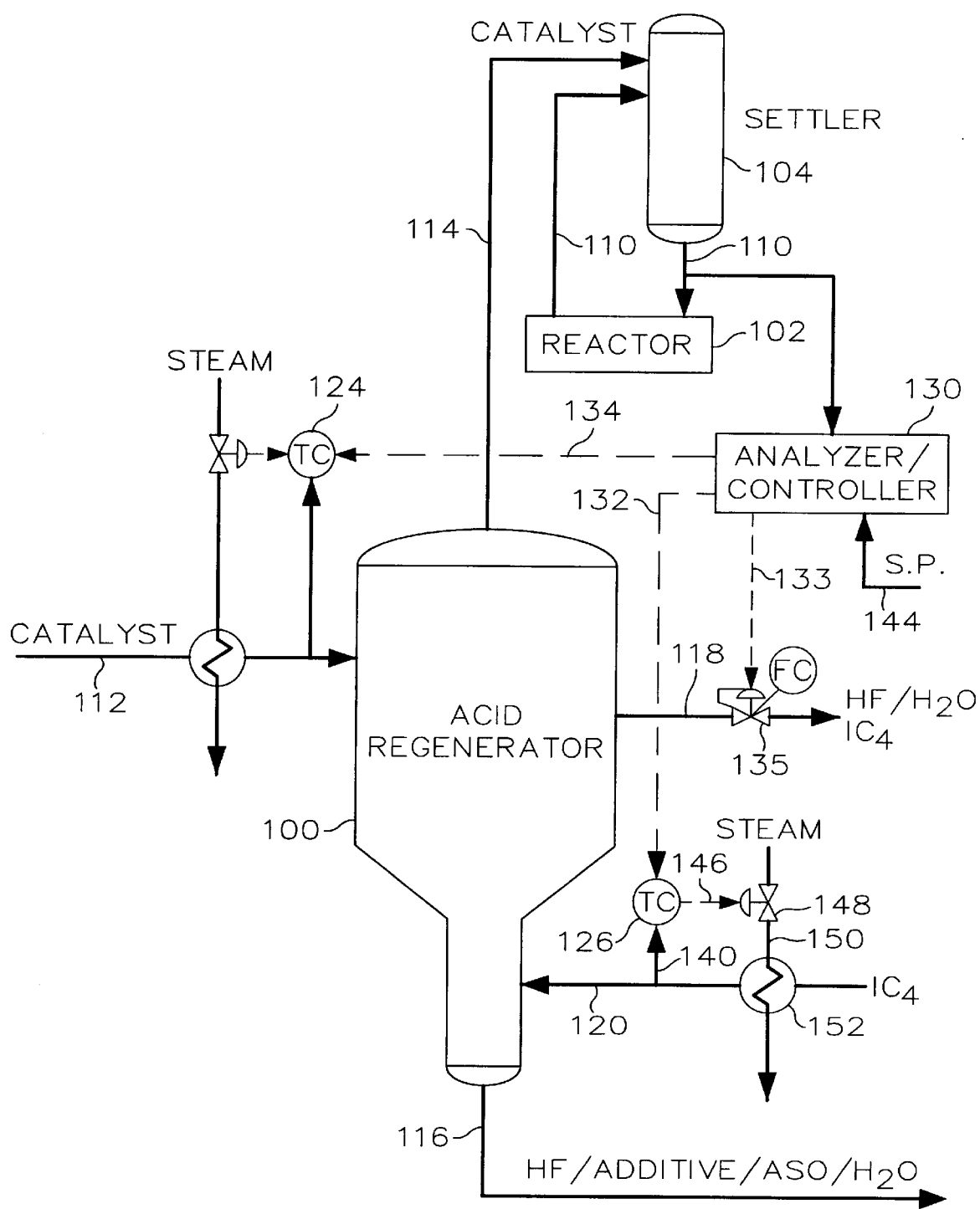
FIG. 8 is a simplified process flow diagram illustrating operational units of an HF alkylation process, and incorporating a control scheme according to the present invention.

A specific control system configuration for an acid catalyst regenerator, which employs an NIR analyzer/controller 130 is set forth in FIG. 8 for the sake of illustration. However, the invention extends to different types of control system configurations which accomplish the purpose of the invention. Lines designated as signal lines, which are showing as dash lines in the drawings, are electrical or pneumatic in this preferred embodiment. Generally the signals provided from any transducer are electric in form.

The invention, however, is also applicable to mechanical, hydraulic or other means for transmitting information. In almost all control systems some combination of electrical, pneumatic, or hydraulic signals will be used. However, the use of any other type of signal transmission compatible with the process and equipment in use is within the scope of the invention.

The PID controllers 124 and 126 shown in FIG. 8 can utilize the various modes of control such as proportional, proportional-integral or proportional-integral-derivative. In the preferred embodiment a proportional-integral mode is utilized. However, any controller having capacity to accept two or more input signals and produce a scaled output signal representative of the comparison of the two input signals is within the scope of the invention.

The scaling of an output signal by a controller is well known in the control systems art. Essentially, the output of a controller can be scaled to represent any desired factor or variable. An example of this is where a desired temperature and an actual temperature are compared by a controller. The controller output might be a signal representative of a flow rate of a "control" gas necessary to make the desired and actual temperatures equal. On the other hand, the same output signal could be scaled to represent a pressure required to make the desired and actual temperatures equal. If the controller output can range from 0–10 units, then the controller output signal could be scaled so that an output having a level of 5 units corresponds to 50% percent or a specified flow rate or a specified temperature. The transducing means used to measure parameters which characterize a process in the various signals generated thereby may take a variety of forms or formats. For example the control elements of this system can be implemented using electrical analog, digital electronic, pneumatic, hydraulic, mechanical, or other similar types of equipment or combination of such types of equipment.

The specific hardware and/or software utilized in such feedback control systems except for the previously described NIR analyzer is well known in the field of process plant control. See for example Chemical Engineering's Handbook, 5th Ed., McGraw-Hill, pgs. 22-1 to 22-147.

Referring now to FIG. 8 which is a simplified schematic illustrating an acid regenerator column 100, a reactor 102, and a settler vessel 104. These vessels are used in an HF alkylation process where a recycle acid catalyst stream recirculates through the reactor 102 and the settler vessel 104 via conduit 110. A portion of this recirculating stream is withdrawn and sent to the regenerator column via conduit 112 where HF acid catalyst, ASO, and $H_2O$ are separated. FIG. 8 also illustrates three possible control loops contemplated for association with the regenerator column. The acid regenerator feed stream in conduit 112, which contains HF acid catalyst, ASO, $H_2O$ and optionally an additive such as sulfolane, is supplied to the regenerator column 100 where a substantial portion of the HF acid catalyst in the feed is removed from the regenerator 100 in an overhead stream via conduit 114. A substantial portion of the ASO and $H_2O$ contained in the feed stream is removed from the regenerator in a bottoms stream via conduit 118. Optionally, a side draw stream in conduit 118 is provided for withdrawing HF acid, $H_2O$ and isobutane. A preheated isobutane stripping fluid is supplied to the lower portion of the regenerator column via conduit 120 for effecting the separation. The analyzer output control signals 132, 133 and 134, which are illustrated as dashed lines in FIG. 8, refer to component concentrations of HF acid, ASO and $H_2O$ in the circulating acid catalyst.

One problem encountered in an HF alkylation process is building up of excessive levels of ASO in the HF acid catalyst stream that is circulated through the reactor in conduit 110. The only way to cause more of the light ASO to drop out of the recirculating acid catalyst in the alkylation process, for removal through the regenerator bottoms stream in conduit 116, is to decrease the temperature of this bottoms stream. A preferred way to decrease this temperature is to decrease the temperature of the stripping isobutane entering the lower portion of the tower in conduit 120. Alternately, decreasing the temperature of the regenerator catalyst feed stream in conduit 112 will decrease the temperature of the bottoms stream, thus increasing the amount of ASO withdrawn in the bottoms stream in conduit 116.

Another benefit for manipulating the temperature of the regenerator bottoms stream in conduit 116 involves maintaining water content in the recirculating catalyst at a desired value. Significant economic benefits can be obtained if the water content of the recirculating catalyst is maintained at 1–2 wt. %. Many refiners, however, do not realize this upgrade because serious corrosion problems occur if the water content should unintentionally rise much above 3 wt. %.

As illustrated in FIG. 8, an output signal 132 from the triple component NIR analyzer/controller 130 is used to control the temperature of the stripping isobutane. In this case, the analyzer output signal used could be representative of either the measured concentrations of ASO or $H_2O$ of the recirculating acid catalyst. As illustrated, however, with connection to temperature controller 126, control signal 132 would be scaled to be representative of the temperature of the isobutane stream in conduit 120 that would maintain the desired concentration of ASO or $H_2O$ in conduit 110 represented by set point signal 144.

Also as illustrated in FIG. 8, the HF/ASO output signal 134 from the NIR analyzer 130 could be used to control the temperature of the catalyst feed to the regenerator in conduit 112 since reducing the catalyst feed temperature also reduces the bottoms temperature so as to increase the amount of HF/ASO withdrawn in the bottoms stream. As illustrated signal 134 would be a scaled control signal.

Another useful control loop in the HF alkylation process, which is also illustrated in FIG. 8, includes manipulating the side draw flow rate in conduit 118 responsive to the measured $H_2O$ concentration in the acid recycle stream, such that a higher side draw flow rate will reduce the $H_2O$ content in the recirculation catalyst stream in conduit 110. This loop would be useful when an additive such as sulfolane is present in the alkylation catalyst.

This on-line concentration measurement and control allows rapid and very close control of critical HF alkylation variables, which results in increased production with close to specification products.

Still referring to FIG. 8 one of the three illustrated candidate control loops will be described in more detail. A temperature transducer such as a thermocouple operably located in conduit 120 provides an output signal 140 which is representative of the actual temperature of liquid flowing in conduit 120. Signal 140 is provided as a first input to the temperature controller 126. Temperature controller 126 is also provided with a set point signal 132, which originates in the NIR analyzer 130, and is a control signal scaled to be representative of the temperature of the stripping isobutane stream in conduit 120 required to maintain the concentration of a component such as ASO in the circulating acid catalyst stream in conduit 110, substantially equal to the desired concentration of the circulating acid stream component represented by set point signal 144.

Responsive to signals 140 and 132 the temperature controller 126 provides an output signal 146 which is representative of the difference between signals 132 and 140. Signal 146 is scaled to be representative of the position of control valve 148, which is operably located in conduit 150, required to maintain the actual temperature in conduit 120 substantially equal to the desired temperature represented by signal 132. Control valve 148 is manipulated responsive to signal 146 so as to adjust steam flow to heat exchanger 152.

In another preferred alternate embodiment NIR analyzer output signal 134 can provide a set point signal for temperature controller 124 which in turn controls the temperature of the acid catalyst feed in conduit 112 so as to maintain a desired concentration of a component in the circulating acid catalyst stream flowing in conduit 110.

Also illustrated in a similar alternate embodiment NIR analyzer output signal 133 could provide a set point signal for pressure controller 135 which is operably located in conduit 118.

While the invention has been described in terms of the presently preferred embodiments, reasonable variations and modifications are possible by those skilled in the art and such modifications and variations are within the scope of the described invention and the appended claims.

That which is claimed is:

1. A method for controlling the separation of chemical components in a circulating stream in an alkylation process containing acid catalyst, acid soluble oil (ASO), and water, wherein a portion of said circulating stream is provided as a feed stream to an acid regenerator column, and wherein a substantial portion of said acid catalyst contained in said feed stream is removed from said acid regenerator column in an overhead stream, and wherein substantial portions of said ASO and said water contained in said feed stream are removed from said acid regenerator column in a bottoms stream, and wherein a hydrocarbon stripping fluid stream is heated by a heating fluid in a heat exchanger and then supplied to a lower portion of said acid regenerator column to effect separations of acid catalyst, ASO, and water, said method comprising the steps of:

(a) analyzing said circulating liquid stream to determine concentration of a chemical component in said circulating stream;

(b) establishing a first signal scaled to be a control signal representative of the temperature of said stripping fluid stream required to maintain a desired concentration of said chemical component in said circulating stream, wherein said first signal is based on the concentration determined in step (a);

(c) providing said first signal as a set point signal to a temperature controller for said stripping fluid;

(d) establishing a second signal representative of the actual temperature of said stripping fluid;

(e) comparing said first signal and said second signal in said temperature controller for said stripping fluid and establishing a third signal responsive to the difference between said first signal and said second signal; and (f) manipulating the flow of said heating fluid to said heat exchanger in response to said third signal to thereby maintain the temperature of said stripping fluid substantially equal to the desired temperature represented by said first signal.

2. A method in accordance with claim 1, wherein said step of analyzing said circulating stream comprises:

using an NIR analyzer to obtain an electromagnetic absorbance spectrum over the near-infrared wavelength range of from about 1250 nm to about 2200 nm.

3. A method in accordance with claim 1 wherein said chemical component in said circulating stream is selected from a group of components consisting of HF acid, ASO, and water.

4. A method in accordance with claim 1 wherein said circulating stream additionally contains an additive.

5. A method in accordance with claim 4, wherein said additive comprises sulfolane.

6. An apparatus comprising:

an alkylation system comprising an alkylation reactor and a settler vessel operably related to said alkylation reactor via a first conduit means for introducing a circulating stream into said settler vessel;

second conduit means operably related to said settler vessel and operably related to said alkylation reactor for introducing said circulating stream into said alkylation reactor;

third conduit means operably related to said second conduit means and operably related to a regenerator column for introducing a portion of said circulating stream as a feed stream to said regenerator column;

fourth conduit means operably related to said regenerator column and operably related to said alkylation system for withdrawing an overhead stream from said regenerator column and for introducing said overhead stream into said alkylation system;

fifth conduit means operably related to said regenerator column for introducing a stripping fluid stream into said regenerator column;

a heat exchanger operably located in said fifth conduit means for transferring heat to said stripping fluid stream;

sixth conduit means operably related to said heat exchanger for introducing a heating fluid to said heat exchanger;

a near infrared (NIR) analyzer means operably related to said second conduit means for determining the actual concentration of a chemical component in said circulating stream, and for establishing a first signal representative of said actual concentration;

means for establishing a second signal representative of the desired concentration of the chemical component in said circulating stream;

computer means for comparing said first signal to said second signal and establishing a third signal representative of the temperature of said stripping fluid stream required to maintain said actual concentration equal to said desired concentration;

means for establishing a fourth signal operably related to said fifth conduit means, down flow from said heat exchanger, representative of the actual temperature of said stripping fluid stream;

means for comparing said third signal and said fourth signal and for establishing a fifth signal which is responsive to the difference between said third signal and said fourth signal; and a control valve operably located in said sixth conduit means for adjusting the flow rate of said heating fluid in response to said fifth signal, wherein said fifth signal is scaled to represent the position of said control valve required to maintain said fourth signal equal to said third signal.

7. An apparatus in accordance with claim 6, wherein said NIR analyzer means records an electromagnetic spectrum over the near-infrared wavelength range of from about 1250 nm to about 2200 nm.

8. An apparatus in accordance with claim 6, wherein said chemical component in said circulating stream is selected from the group of components consisting of HF acid, ASO and water.

9. An apparatus in accordance with claim 8, wherein said circulating stream additionally contains an additive.

10. An apparatus in accordance with claim 9, wherein said additive comprises sulfolane.

11. A method for controlling the separation of chemical components in a circulating stream in an alkylation process containing acid catalyst, acid soluble oil (ASO), and water, wherein a portion of said circulating stream is provided as a feed stream to an acid regenerator column, and wherein a substantial portion of said acid catalyst contained in said feed stream is removed from said acid regenerator column in an overhead stream, and wherein substantial portions of said ASO and said water contained in said feed stream are removed from said acid regenerator column in a bottoms stream, and wherein said feed stream is heated by a heating fluid in a heat exchanger and then supplied to said acid regenerator column to effect separations of acid catalyst, ASO, and water, said method comprising the steps of:

(a) analyzing said circulating stream to determine concentration of a chemical component in said circulating stream;

(b) establishing a first signal scaled to be a control signal representative of the temperature of said feed stream required to maintain a desired concentration of said chemical component in said circulating stream, wherein said first signal is based on the concentration determined in step (a);

(c) providing said first signal as a set point signal to a temperature controller for said feed stream;

(d) establishing a second signal representative of the actual temperature of said feed stream;

(e) comparing said first signal and said second signal in said temperature controller for said feed stream and establishing a third signal responsive to the difference between said first signal and said second signal; and (f) manipulating the flow of said heating fluid to said heat exchanger in response to said third signal to thereby maintain the temperature of said feed stream substantially equal to the desired temperature represented by said first signal.

12. A method in accordance with claim 11, wherein said step of analyzing said circulating stream comprises:

using an NIR analyzer to obtain an electromagnetic absorbance spectrum over the near-infrared wavelength range of from about 1250 nm to about 2200 nm.

13. A method in accordance with claim 11, wherein chemical component in said circulating stream is selected from a group of components consisting of HF acid, ASO, and water.

14. A method in accordance with claim 11 wherein said circulating stream additionally contains an additive.

15. A method in accordance with claim 14, wherein said additive comprises sulfolane.

16. An apparatus comprising:
an alkylation system comprising an alkylation reactor and a settler vessel operably related to said alkylation reactor via a first conduit means for introducing a circulating stream into said settler vessel;
second conduit means operably related to said settler vessel and operably related to said alkylation reactor for introducing said circulating stream into said alkylation reactor,
third conduit means operably related to said second conduit means and operably related to a regenerator column for introducing a portion of said circulating stream as a feed stream to said regenerator column;
fourth conduit means operably related to said regenerator column and operably related to said alkylation system for withdrawing an overhead stream from said regenerator column and for introducing said overhead stream into said alkylation system;
a heat exchanger operably located in said third conduit means for transferring heat to said feed stream;
fifth conduit means operably related to said heat exchanger for introducing a heating fluid to said heat exchanger;
a near infrared (NIR) analyzer means operably related to said second conduit means for determining the actual concentration of a chemical component in said circulating stream, and for establishing a first signal representative of said actual concentration;
means for establishing a second signal representative of the desired concentration of the chemical component in said circulating stream;
computer means for comparing said first signal to said second signal and establishing a third signal representative of the temperature of said feed stream required to maintain said actual concentration equal to said desired concentration;
means for establishing a fourth signal operably related to said third conduit means, down flow from said heat exchanger, representative of the actual temperature of said feed stream;
means for comparing said third signal and said fourth signal and for establishing a fifth signal which is responsive to the difference between said third signal and said fourth signal; and
a control valve operably located in said fifth conduit means for adjusting the flow rate of said heating fluid in response to said fifth signal, wherein said fifth signal is scaled to represent the position of said control valve required to maintain said fourth signal equal to said third signal.

17. An apparatus in accordance with claim 16, wherein said NIR analyzer means records an electromagnetic spectrum over the near-infrared wavelength range of from about 1250 nm to about 2200 nm.

18. An apparatus in accordance with claim 16, wherein said chemical component in said circulating stream is selected from the group of components consisting of HF acid, ASO and water.

19. An apparatus in accordance with claim 18, wherein said circulating stream additionally contains an additive.

20. An apparatus in accordance with claim 19, wherein said additive comprises sulfolane.

21. A method for controlling the separation of chemical components in a circulating stream in an alkylation process containing acid catalyst, acid soluble oil (ASO), and water, wherein a portion of said circulating stream is provided as a feed stream to an acid regenerator column, and wherein a substantial portion of said acid catalyst contained in said feed stream is removed from said acid regenerator column in an overhead stream, and wherein substantial portions of said ASO and said water contained in said feed stream are removed from said acid regenerator column in a bottoms stream, and wherein a side draw comprising water is removed from said acid regenerator column to effect separations of acid catalyst, ASO, and water, said method comprising the steps of:
(a) analyzing said circulating stream to determine concentration of a chemical component in said circulating stream;
(b) establishing a first signal scaled to be a control signal representative of the flow rate of said side draw required to maintain a desired concentration of said chemical component in said circulating stream, wherein said first signal is based on the concentration determined in step (a);
(c) providing said first signal as a set point signal to a flow controller for said side draw;
(d) establishing a second signal representative of the actual flow rate of said side draw;
(e) comparing said first signal and said second signal in said flow controller for said side draw and establishing a third signal responsive to the difference between said first signal and said second signal; and
(f) manipulating the flow of said side draw in response to said third signal to thereby maintain the flow rate of said side draw substantially equal to the desired flow rate represented by said first signal.

22. A method in accordance with claim 21, wherein said step of analyzing said circulating stream comprises:
using an NIR analyzer to obtain an electromagnetic absorbance spectrum over-the near-infrared wavelength range of from about 1250 nm to about 2200 nm.

23. A method in accordance with claim 21 wherein said chemical component in said circulating stream is selected from a group of components consisting of HF acid, ASO, and water.

24. A method in accordance with claim 21 wherein said circulating stream additionally contains an additive.

25. A method in accordance with claim 24, wherein said additive comprises sulfolane.

26. An apparatus comprising:
an alkylation system comprising an alkylation reactor and a settler vessel operably related to said alkylation reactor via a first conduit means for introducing a circulating stream into said settler vessel;
second conduit means operably related to said settler vessel and operably related to said alkylation reactor for introducing said circulating stream into said alkylation reactor;
third conduit means operably related to said second conduit means and operably related to a regenerator column for introducing a portion of said circulating stream as a feed stream to said regenerator column;
fourth conduit means operably related to said regenerator column and operably related to said alkylation system for withdrawing an overhead stream from said regenerator column and for introducing said overhead stream into said ablation system;
fifth conduit means operably related to said regenerator column for withdrawing a side draw from said regenerator column;

a near infrared (NIR) analyzer means operably related to said second conduit means for determining the actual concentration of a chemical component in said circulating stream, and for establishing a first signal representative of said actual concentration;

means for establishing a second signal representative of the desired concentration of the chemical component in said circulating stream;

computer means for comparing said first signal to said second signal and establishing a third signal representative of the flow rate of said side draw required to maintain said actual concentration equal to said desired concentration;

means for establishing a fourth signal operably related to said fifth conduit means, representative of the actual flow rate of said side draw;

means for comparing said third signal and said fourth signal and for establishing a fifth signal which is responsive to the difference between said third signal and said fourth signal; and a control valve operably located in said fifth conduit means for adjusting the flow rate of said side draw in response to said fifth signal, wherein said fifth signal is scaled to represent the position of said control valve required to maintain said fourth signal equal to said third signal.

27. An apparatus in accordance with claim 26, wherein said NIR analyzer means records an electromagnetic spectrum over the near-infrared wavelength range of from about 1250 nm to about 2200 nm.

28. An apparatus in accordance with claim 26, wherein said chemical component in said circulating stream is selected from the group of components consisting of HF acid, ASO and water.

29. An apparatus in accordance with claim 28, wherein said circulating stream additionally contains an additive.

30. An apparatus in accordance with claim 29, wherein said additive comprises sulfolane.

* * * * *

UNITED STATES PATENT AND TRADEMARK OFFICE
CERTIFICATE OF CORRECTION

PATENT NO. : 6,228,650 B1
DATED : May 8, 2001
INVENTOR(S) : William P. Moore, Mark A. Clark, Bruce B. Randolph It is certified that error appears in the above-identified patent and that said Letters Patent is hereby corrected as shown below:

Column 9, claim 16,
Line 9, please delete "," and insert therefor -- ; --.

Signed and Sealed this

Twenty-sixth Day of March, 2002

*Attest:*

*Attesting Officer*

JAMES E. ROGAN
*Director of the United States Patent and Trademark Office*